United States Patent
Kaminski (10) Patent No.: US 10,996,223 B2
(45) Date of Patent: May 4, 2021

(54) SCREENING METHOD FOR DIAGNOSIS OF HAEMATOLOGICAL NEOPLASIA

(71) Applicant: Wolfgang Kaminski, Schriesheim (DE)

(72) Inventor: Wolfgang Kaminski, Schriesheim (DE)

(73) Assignee: Bioscientia Institut Für Medizinische Diagnostik GmbH, Ingelheim (DE)

( * ) Notice: Subject to any disclaimer, the term of this patent is extended or adjusted under 35 U.S.C. 154(b) by 0 days.

(21) Appl. No.: 16/727,645

(22) Filed: Dec. 26, 2019

(65) Prior Publication Data

US 2020/0132692 A1    Apr. 30, 2020

Related U.S. Application Data

(63) Continuation of application No. PCT/EP2018/067075, filed on Jun. 26, 2018.

(30) Foreign Application Priority Data

Jun. 26, 2017    (EP) ..................................... 17177870

(51) Int. Cl.
| | | |
|---|---|---|
| G01N 33/574 | (2006.01) | |
| G16H 50/20 | (2018.01) | |
| G01N 33/569 | (2006.01) | |
| G01N 33/72 | (2006.01) | |

(52) U.S. Cl.
CPC . *G01N 33/57426* (2013.01); *G01N 33/56972* (2013.01); *G01N 33/721* (2013.01); *G16H 50/20* (2018.01)

(58) Field of Classification Search
CPC ....... G01N 33/57426; G01N 33/56972; G01N 33/721; G16H 50/20
USPC .......................................................... 702/19
See application file for complete search history.

(56) References Cited

U.S. PATENT DOCUMENTS

2010/0009364 A1    1/2010    Fantl et al.

FOREIGN PATENT DOCUMENTS

| WO | WO 2013/009690 A2 | 1/2013 |
|---|---|---|
| WO | WO 2015/119570 A1 | 8/2015 |
| WO | WO 2016/144728 A2 | 9/2016 |
| WO | WO 2016/196580 A1 | 12/2016 |

OTHER PUBLICATIONS

Jan Cerny et al., "Why Does My Patient Have Leukocytosis?", Hematology—Oncology Clinics of North America, US, vol. 26, No. 2, Feb. 17, 2012, pp. 303-319, 17 pages.
D. Oscier et al., "Guidelines on the diagnosis and management of chronic lymphocytic leukaemia", British Journal of Haematology, GB, vol. 125, No. 3, May 1, 2004, pp. 294-317, 24 pages.
F. E. Craig, "The utility of peripheral blood smear review for identifying specimens for flow cytometric immunophenotyping", International Journal of Laboratory Hematology, GB; US, vol. 39, Apr. 26, 2017, pp. 41-46, 6 pages.
David J. Foran et al., "Computer-Assisted Discrimination Among Malignant Lymphomas and Leukemia Using Immunophenotyping, Intelligent Image Repositories, and Telemicroscopy", IEEE Transactions on Information Technology in Biomedicine, IEEE Service Center, Los Alamitos, California, U.S., vol. 4, No. 4, Dec. 1, 2000, 9 pages.
Wang Endi et al., "An Epstein-Barr virus-positive diffuse large B-cell lymphoma presenting as multi-organ failure: A catastrophic lymphomatosis with fulminant visceral organ dissemination resulting in a precipitous death in a 59-year-old female with no identifiable etiology for immunodefici", Pathology—Research and Practice, Elsevier, Amsterdam, Netherlands, vol. 210, No. 1, Sep. 17, 2013, 5 pages.
O Hrodek et al., "Prognostic criteria and staging in ALL in childhood", Haematologia, vol. 10, Jan. 1, 1976, pp. 33-39, 7 pages.

*Primary Examiner* — Jerry Lin
(74) *Attorney, Agent, or Firm* — Reinhart Boerner Van Deuren P.C.

(57) ABSTRACT

Embodiments of the disclosure relate to a screening method for the diagnosis of haematological neoplasia. In the method, a first test step is performed to check whether a potential haematological neoplasia exists. At least a first haematogram is created with a blood sample in the first test step. Based on a first set of filter rules, it is checked whether the first haematogram differs from a desired state specified according to the first set of filter rules, and a second test step is performed to check for potential haematological neoplasia if the first test step reveals that there is potential haematological neoplasia. In addition, the disclosure relates to a system, a computer program product, and a computer-readable storage medium.

18 Claims, 4 Drawing Sheets

Fig.4

SCREENING METHOD FOR DIAGNOSIS OF HAEMATOLOGICAL NEOPLASIA

CROSS-REFERENCE TO RELATED PATENT APPLICATION

This patent application is a continuation of PCT/EP2018/067075, filed Jun. 26, 2018, which claims priority to European Application No. 17177870.7, filed Jun. 26, 2017, the entire teachings and disclosure of which are incorporated herein by reference thereto.

FIELD

The present invention relates to a screening method for the diagnosis of haematological neoplasia. Furthermore, the invention also relates to a system, a computer program product and a storage medium.

BACKGROUND

From the prior art it is known to diagnose diseases or potential diseases by means of a blood screening method in the laboratory. Also, in the field of cancers, such as in prostate or colon cancer, it is known to perform screening methods that allow a systematic early detection of the disease.

However, such a method does not exist in the area of cancer of the hematopoietic or lymphatic system (hereinafter also referred to as "blood cancer"), although in Germany, for example, approximately 35,000 individuals of each age group contract it annually. Essentially, a distinction is made between the two main groups "leukaemia" and "lymphoma" and currently between a total of 173 different types of blood cancer. The problem is that the disease initially goes unnoticed and only at an advanced stage leads to tangible disease symptoms that manifest clinically. To make matters worse, even then the symptoms caused and the laboratory findings are non-specific and are difficult to distinguish from much more common diseases. The high number of blood cancers and the lack of or non-specific symptoms mean that no reliable screening method for the detection of blood cancer exists. As a result, the blood cancer usually remains unrecognised for a long time and is recognised only very late and therefore at an advanced stage by the doctor. Earlier and thus possibly life-saving therapies cannot be reliably provided for this type of cancer. Rather, the diagnosis of blood cancer in the current practice is not infrequently an incidental finding, mostly based on a markedly conspicuous laboratory finding, as typically occurs only at a very advanced stage. The diagnosis of blood cancer in the current state of the art is thus complicated, time consuming, costly and requires proven expertise.

Systematic screening methods for blood cancer on samples from large groups of patients, such as those found in a large-scale laboratory every day, for example, have not been feasible for these reasons. In particular, it has not yet been possible to establish a method with criteria with which samples of healthy and ill persons with respect to haematological neoplasia could be correspondingly identified, i.e. in particular where false-positive and false-negative diagnoses were reduced to a minimum or avoided.

BRIEF SUMMARY

Against this background, the object now is to specify a screening method which allows efficient and effective, that is, in particular cost-effective, fast and reliable, diagnosis of a (potential) haematological neoplasia.

The object is achieved according to a first aspect of the invention by a screening method for the diagnosis of haematological neoplasia, comprising the steps:

performing a first test step to check for potential haematological neoplasia, wherein at least a first haematogram is created with a blood sample as part of the first test step and it is checked based on a first set of filter rules whether the first haematogram deviates from a desired state specified according to the first set of filter rules, and performing a second test step to check for potential haematological neoplasia if the test in the first step indicates that there is a potential haematological neoplasia.

In accordance with the invention, it was first recognised that the diagnosis of haematological neoplasia becomes accessible by means of an effective and efficient systematic screening method, by dividing the method into at least a first and a second test step. In each test step it is checked whether there is a potential haematological neoplasia. If the first test step already indicates that there is no haematological neoplasia, the second test step, for example, no longer needs to be performed. In any case, the first test step comprises the creation of a first haematogram with a blood sample. The invention proposes, on the basis of a first set of filter rules, checking whether the first haematogram deviates from a desired state, which is specified according to the first set of filter rules. It has been found that the definition of a set of filter rules in a first test step, which precedes a second test step, enables an efficient and effective check for the presence of a potential haematological neoplasia.

In particular, it has been found that it is even possible to reduce the number of blood samples that must be subjected to the second test step to less than 1% of the number of blood samples that still pass through the first test step. In addition, the second test step allows the number of blood samples to be subjected to further testing to continue to be reduced to about 2% of the blood samples undergoing the second test step. In this way, the diagnosis of haematological neoplasia can be realised as part of a mass screening.

The method can thus be understood in particular as a systematic method for multistage (mass) screening, which comprises at least a first and a second test step. However, it is not excluded that the process may include further upstream, downstream, and/or intermediate test steps.

Haematological neoplasia is understood to mean, in particular, malignant neoplasms, as occur in leukaemias or lymphomas.

The blood sample is preferably an (EDTA) whole blood sample. The first haematogram is preferably created on the basis of a blood sample in the liquid phase. The first haematogram may, in particular, be a small or complete blood count, but preferably a small blood count. It has been found that the accuracy achieved thereby is sufficient for the test to be carried out, which in turn allows a particularly high efficiency in terms of time and cost. As part of the first test step, in particular also a further haematogram can be created as will be explained in more detail below.

In one example, the first test step merely involves the creation of a first haematogram. In this case, it is then preferably decided that, according to the first test step, there is a potential haematological neoplasia when the first haematogram deviates from the desired state specified according to the first set of filter rules. If, for example, the first test step also comprises the creation of a second haematogram, it is preferably decided in this case that, according to the first test step, there is a potential haematological neoplasia if the second haematogram differs from the desired state specified according to the first set of filter rules. The fact that the first haematogram deviates from the desired state specified according to the first set of filter rules in this case merely results, for example, in the fact that initially the second haematogram is created, which will also be described in more detail below.

Preferably, the set of filter rules specifies a desired state, while, moreover, each filter rule of the set of filter rules also specifies a respective desired state. Thus, for example, the first haematogram deviates from a desired state specified according to the first set of filter rules, if the first haematogram deviates for example according to only a single filter rule, according to a plurality of filter rules or only according to all filter rules of the first set of filter rules of the first test step from the desired state specified by the respective filter rule(s). As will be described below, however, it is preferred if a deviation is already sufficient according to a single filter rule of the first set of filter rules to determine that the first haematogram deviates from a desired state specified according to the first set of filter rules.

In particular, one or more blood values are determined by the haematogram. For example, a filter rule specifies a desired state, in particular with regard to one or more of the blood values determined in the context of the haematogram. In particular, a blood value may be information on the quantity (for example, a relative or absolute amount) of a (cellular) blood constituent.

The first test step can preferably be carried out partially or completely automatically, for example by a system according to the second aspect. In particular, for creating and/or testing the first haematogram, a first automatic cell analyser may be provided.

The first set of filter rules preferably includes multiple filter rules. Preferably, the first set of filter rules comprises at least two filter rules. Preferably, the first set of filter rules comprises at most ten, preferably at most five filter rules. Particularly preferably, the first set of filter rules comprises exactly four filter rules. Each filter rule can be based, for example, on one or more blood values of the haematogram.

According to a preferred embodiment of the screening method according to the first aspect, as part of the first test step, if the first haematogram deviates from the desired state specified according to the first set of filter rules, a second haematogram, which has a higher accuracy than the first, is created with the blood sample, and based on the first set of filter rules it is checked whether the second haematogram deviates from the desired state specified according to the first set of filter rules. It has been found that this can be highly effective in further increasing the efficiency of the process. Particularly advantageously in this case, the first haematogram is a small blood count while the second haematogram is a complete blood count. To create and/or check the second haematogram, a second automatic cell analyser (with a higher accuracy than the first one) may also be provided.

As already mentioned, in this embodiment, the second haematogram is created when the first haematogram deviates from the desired state specified according to the first set of filter rules. If the second haematogram then differs from the desired state specified according to the first set of filter rules, it is preferably decided that there is a potential haematological neoplasia according to the first test step. In this regard, the statements in relation to the first haematogram apply. Thus, in particular, the second haematogram preferably already deviates from a desired state specified according to the first set of filter rules when the second haematogram deviates, for example, according to only one single filter rule of the first set of filter rules of the first test step, from the desired state specified by the respective filter rule.

Both the first haematogram and the second haematogram are checked in this case on the basis of the first set of filter rules. In principle, however, it would also be conceivable that different sets of filter rules are used for the first and second haematograms.

According to a preferred embodiment of the screening method according to the first aspect, the at least first haematogram (and optionally the second haematogram) already deviates from the desired state specified according to the first set of filter rules when the at least first haematogram deviates from a desired state specified according to a filter rule of the first set of filter rules. It has been found that as part of the first test step, in a set of filter rules, it is advantageous in terms of effective and efficient screening, to already assume a deviation of the first and optionally second haematogram from the desired state specified by the entire set of filter rules, if this is the case according to one filter rule.

According to a preferred embodiment of the screening method according to the first aspect, the at least first haematogram (and optionally the second haematogram) comprises an 'abnormal lymphocytes' value, an 'immature granulocytes' value and/or a blast value, wherein a filter rule of the first set of filter rules of the first test step is based on the 'abnormal lymphocytes' value, the 'immature granulocytes' value and/or the blast value. It has been found that a first set of filter rules, including a filter rule based on the 'abnormal lymphocytes' value, the 'immature granulocytes' value and/or the blast value, is advantageous in terms of high effectiveness and efficiency of the first step. For example, this filter rule may be referred to as the first filter rule. The respective blood values may in particular include information on the quantity (for example a presence or a relative or absolute amount) of the respective blood constituent. Preferably, the filter rule is based on the 'abnormal lymphocytes' value, the 'immature granulocytes' value and the blast value, that is on all three of the above blood values. Preferably, at least the first haematogram deviates from the desired state specified according to this filter rule if either abnormal lymphocytes or immature granulocytes or blasts are present. The same applies to an optionally second haematogram of the first test step.

According to a preferred embodiment of the screening method according to the first aspect, the at least first haematogram (and optionally the second haematogram) comprises a leucocytes value, wherein a filter rule of the first set of filter rules of the first test step is based on the leucocytes value. It has been found that a first set of filter rules comprising a filter rule based on the leucocytes value is advantageous in terms of high effectiveness and efficiency of the first test step. This filter rule may, for example, be referred to as a second filter rule. In particular, the leucocytes value may include information on the quantity (for example a relative or absolute amount, for example number/volume) of the leucocytes. The same applies to an optionally second haematogram of the first test step.

According to a preferred embodiment of the screening method according to the first aspect, the at least first haematogram (and optionally the second haematogram) deviates from the desired state specified according to the filter rule based on the leucocytes value (second filter rule) of the first test step when the leucocytes value is above a threshold or corresponds to this. The leucocytes value is understood to mean, in particular, a total value with regard to all leucocytes. Preferably, the threshold is greater than 40,000, preferably greater than 45,000 leucocytes/µL. Preferably, the threshold is less than 200,000, preferably less than 100,000 leucocytes/µL. Preferably, the threshold is about 50,000 leucocytes/ΞL.

According to a preferred embodiment of the screening method according to the first aspect, the at least first haematogram (and optionally the second haematogram) comprises a haemoglobin value and a platelets value, wherein a filter rule of the first set of filter rules of the first test step is based on the haemoglobin value and the platelets value. It has been found that a first set of filter rules, including a filter rule based on the haemoglobin value and platelets value, is advantageous in terms of high effectiveness and efficiency of the first test step. This filter rule may be referred to, for example, as a third filter rule. In particular, the respective blood value may comprise information on the quantity (for example a relative or absolute quantity, for example number/volume) of the respective blood constituent. The same applies to an optionally second haematogram of the first test step.

According to a preferred embodiment of the screening method according to the first aspect, the at least first haematogram (and optionally the second haematogram) deviates from the desired state specified according to the filter rule based on the haemoglobin value and platelets value (third filter rule) of the first test step, if the haemoglobin value is below a threshold or corresponds to this and the platelets value is below or corresponds to a threshold value. It has been found to be particularly advantageous in terms of the effectiveness and efficiency of the method if it is checked whether both the haemoglobin value is below a threshold and the platelets value is below a threshold. Preferably, the threshold for the haemoglobin value is greater than 8 g/dl. Preferably, the threshold for the haemoglobin value is less than 14 g/dl. Preferably, the threshold for the haemoglobin value is between 10 and 12.5 g/dl. Preferably, the threshold for the platelets value is greater than 80,000, more preferably greater than 90,000 platelets/µL. Preferably, the threshold for the platelets value is less than 120,000, more preferably less than 110,000 platelets/µL. Preferably, the threshold for the platelets value is approximately 100,000 platelets/µL.

According to a preferred embodiment of the screening method according to the first aspect, the threshold for the haemoglobin value is a gender-specific threshold. As a result, the effectiveness and efficiency of the filter based thereon (third filter rule) can be further increased. In other words, the threshold for the haemoglobin value depends on the gender of the person from whom the blood sample was taken. For females (or for blood samples where the gender of the person is not known), the threshold for the haemoglobin value is preferably greater than 8 g/dl and/or preferably less than 12 g/dl, in particular approximately 10.6 g/dl. In males, the threshold for the haemoglobin value is preferably greater than 10 g/dl and/or preferably less than 14 g/dl, and in particular is about 12.1 g/dl.

According to a preferred embodiment of the screening method according to the first aspect, the at least first haematogram (and optionally the second haematogram) comprises a monocytes value, wherein a filter rule of the first set of filter rules of the first test step is based on the monocytes value. It has been found that a first set of filter rules comprising a filter rule based on the monocytes value is advantageous in terms of high effectiveness and efficiency of the first test step. This filter rule may be referred to as a fourth filter rule, for example. In particular, the monocytes value may include information on the quantity (for example a relative or absolute amount, for example number/volume) of the monocytes. The same applies to an optionally second haematogram of the first test step.

According to a preferred embodiment of the screening method according to the first aspect, the at least first haematogram (and possibly the second haematogram) deviates from the desired state specified according to the filter rule based on the monocytes value (fourth filter rule) of the first test step if the monocytes value is above a threshold value or corresponds thereto. Preferably, the threshold is greater than 1,250 monocytes/µL. Preferably, the threshold is less than 1,750 monocytes/µL. Preferably, the threshold is approximately 1,500 monocytes/µL.

In particular, a combination of at least (preferably exactly) the four filter rules described above has proved to be particularly advantageous for an effective and efficient first test step and for use in mass screening with a high number of blood samples to be tested.

According to a preferred embodiment of the screening method according to the first aspect, a morphological analysis result of a solid phase of the blood sample is determined as part of the second test step and it is checked based on a second set of filter rules whether the morphological analysis result of the second test step deviates from a desired state specified according to the second set of filter rules.

By carrying out the second test step only if the first test step indicates that there is potential haematological neoplasia, the number of samples to be tested in the second test step can be significantly reduced. As already described, a situation in which only approximately 1% of the original blood samples need to be subjected to the second test step can be achieved. This makes it possible in the second test step, compared to the first step, for a more complex morphological analysis result of a solid phase of the blood sample (e.g. based on a blood cell solid phase carrier, which can be generated for instance by a blood smear, by nozzle-applied blood or otherwise) to be determined and used in the testing. By providing a morphological analysis in the second test step, the effectiveness can be further improved while maintaining the high efficiency of the screening method.

The second test step can preferably be carried out partially or completely automatically, for example by a system according to the second aspect.

In particular, a device for automatic production of a solid phase of the blood sample and/or a device for morphological analysis (digital cell morphology analyser) may be provided. In addition, the results from the morphological analysis device can also be manually sorted or corrected.

The solid phase of the blood sample is prepared in particular by means of whole blood. Preferably, the blood cell solid phase generated in this way is dyed.

For example, it is decided in the second test step that a potential haematological neoplasia exists if the morphological analysis result of the second test step deviates from a desired state specified according to the second set of filter rules. This may be the case in particular if no further testing is carried out as part of the second test step.

As already stated with regard to the first set of filter rules, the second set of filter rules also specifies a desired state, while each filter rule of the second set of filter rules also specifies in itself a desired state in each case. Thus, for example, the morphological analysis result deviates from a desired state specified according to the second set of filter rules, if the morphological analysis result according to just a single filter rule, according to a plurality of filter rules or only according to all the filter rules of the second set of filter rules of the second test step deviates from the desired state specified by the respective filter rule(s). As will be described below, however, it is preferred if a deviation already according to a single filter rule of the second set of filter rules is sufficient to determine that the morphological analysis result deviates from a desired state specified according to the second set of filter rules.

Similar to the first set of filter rules, the second set of filter rules also preferably includes multiple filter rules. However, the second set of filter rules preferably differs from the first set of filter rules. Preferably, the second set of filter rules comprises at least two, preferably at least five filter rules. Preferably, the second set of filter rules comprises at most 20, preferably at most 15 filter rules. Particularly preferably, the second set of filter rules comprises exactly ten filter rules. Each filter rule can be based, for example, on one or more blood values.

According to a preferred embodiment of the screening method according to the first aspect, the morphological analysis result of the second test step already deviates from the desired state specified according to the second set of filter rules if the morphological analysis result of the second test step deviates from a desired state specified according to a filter rule of the second set of filter rules. It has been found that it is also advantageous as part of the second test step, for a set of filter rules, with regard to an effective and efficient screening, to already assume a deviation of the morphological analysis result from the desired state specified by the entire set of filter rules if this is the case according to one filter rule.

According to a preferred embodiment of the screening method according to the first aspect, the morphological analysis result of the second test step comprises one or more cell type values, in particular nucleated cell types, wherein one or more filter rules of the second set of filter rules of the second test step are each based on at least one, in particular exactly one, cell type value.

In particular, a respective cell type value may be information on the quantity (for example, a relative or absolute amount) of a respective cell type. For example, each of the filter rules of the second set of filter rules refers to another cell type, particularly a nucleated cell type. Preferably, one or more (preferably all) of the cell type values are nucleated cell type values. Preferably, all filter rules of the second set of filter rules are based on at least one, preferably exactly one, cell type value, in particular a nucleated cell type value.

According to a preferred embodiment of the screening method according to the first aspect, the morphological analysis result of the second test step deviates from the desired state specified according to a filter rule based on a cell type value of the second test step, if the respective cell type value is above or corresponds to a respective threshold value. As a rule, there is a specific threshold value for each cell type value.

According to a preferred embodiment of the screening method according to the first aspect, it has been found to be advantageous with regard to the effectiveness and efficiency of the second test step if one or more of the cell type values is based on the following cell types:
shadow cells;
likely reactive atypical lymphocytes;
lymphocytes;
unclear and/or neoplastic lymphocytes;
monocytes;
basophilic granulocytes;
myelocytes;
promyelocytes;
blasts; or
normoblasts.

Preferably, there is at least one, preferably exactly one, filter rule in the second set of filter rules for each cell type. Preferably, the second set of filter rules therefore comprises at least ten filter rules, wherein each filter rule is in each case preferably based on one cell type value.

The shadow cell type is understood to be leucocytes, which were crushed in the preparation of the solid phase of the blood sample and represent themselves as structureless blurs of colour.

For 100 counted nucleated cells, the respective thresholds are preferably as follows:

Preferably, the threshold value for the "shadow cell" cell type (shadow cell value) is greater than 5, preferably (at least) 10.

Preferably, the threshold for the "likely reactive atypical lymphocytes" cell type (likely reactive atypical lymphocytes' value) is greater than 10, preferably (at least) 15.

Preferably, the threshold value for the "lymphocytes" cell type (lymphocytes value) is greater than 60, preferably (at least) 70.

The threshold for the "unclear and/or neoplastic lymphocytes" cell type ('unclear and/or neoplastic lymphocytes' value) is preferably (at least) 1.

Preferably, the threshold value for the "monocytes" cell type (monocytes value) is greater than 15, preferably (at least) 20.

The threshold for the "basophilic granulocytes" cell type ('basophilic granulocytes' value) is preferably (at least) 5.

The threshold for the "myelocytes" cell type (myelocytes value) is preferably (at least) 5.

The threshold for the "promyelocytes" cell type (promyelocytes value) is preferably (at least) 3.

The threshold for the "blast" cell type (blast value) is preferably (at least) 3.

The threshold for the "normoblasts" cell type (normoblasts value) is preferably (at least) 5.

The threshold values given above for the individual cell types have proved to be advantageous filter rules in the second test step (in particular in combination).

According to a preferred embodiment of the screening method according to the first aspect, as part of the second test step, the plasma (for example the plasma values) and/or the serum (for example the serum values) of the blood sample and/or the urine are checked for haematological neoplasia. For example, as part of the second test step, the plasma values and/or serum values of the blood sample and/or urine are always checked for haematological neoplasias when a sample is present with the plasma or serum or urine. Alternatively or additionally, as part of the second test step one or more other body fluids (which may also include semi-fluid material) may be used in testing for haematological neoplasia. Thus, in particular, alternatively or in addition to blood-based body fluids (such as plasma, serum), non-blood-based body fluids are used, such as secretions, excreta and/or fluid excretion (for example, an examination of the urine already mentioned). For example, the body fluid may be a punctate or an aspirate (for example, a fluid or semi-fluid material of a body cavity, such as the abdomen or the pleural space).

If, during the second test step, the plasma and/or serum of the blood sample and/or urine is tested for haematological neoplasia, for example in the second test step, both on the basis of the morphological evaluation and on the result of the plasma and/or serum and/or urine test, it is decided whether a potential haematological neoplasia is present.

According to a second aspect of the invention, a system is also described which is configured or comprises corresponding means for carrying out and/or controlling a method according to the first aspect. The system can, for example, include one or more devices. An exemplary device comprises, for instance, a data processing system that is configured in terms of software and/or hardware in order to be able to carry out the respective steps of an exemplary method according to the first aspect. Examples of a data processing system include a computer, a desktop computer, a server, a thin client and/or a portable computer. By way of example, the system comprises devices in the form of a first and optionally a second automatic cell analyser for the first test step. By way of example, the system comprises a device in the form of a digital cell morphology analyser and/or a device for automatically preparing the solid phase of the blood sample for the second test step.

For example, an exemplary device further includes means for storing information such as a program memory and/or main memory. For example, an exemplary device according to the invention further includes means for receiving and/or transmitting information over a network, such as a network interface. For example, exemplary devices are interconnected and/or connectable via one or more networks.

According to a preferred embodiment of the second aspect, the system comprises at least one processor and at least one memory with computer program code, wherein the at least one memory and the computer program code are configured to at least execute and/or control the process with the at least one processor. A processor means, for example, a control unit, a microprocessor, a micro-control unit such as a microcontroller, a Digital Signal Processor (DSP), an Application Specific Integrated Circuit (ASIC) or a Field Programmable Gate Array (FPGA).

According to a third aspect of the invention, a computer program product is also described, comprising:
program instructions for executing a method according to the first aspect when the program instructions are executed on a processor.

According to a fourth aspect of the invention, a computer-readable storage medium containing a computer program product according to the third aspect of the invention is also described. An exemplary program according to the invention may be stored in or on a computer-readable storage medium containing one or more exemplary programs, and e.g. is designed as a magnetic, electrical, electro-magnetic, optical and/or other type of storage medium. Such a computer-readable storage medium is preferably tangible (i.e. "touchable"), for example it is formed as a data carrier device. Such a data carrier device is for example portable or permanently installed in a device. Examples of such a data carrier device are a volatile or non-volatile random access memory (RAM) such as e.g. a NOR flash memory or one with sequential access such as a NAND flash memory and/or a read only access (ROM) memory or with read/write access. For example, computer-readable shall be understood to mean that the storage medium can be read (and/or written to) by a computer or a data processing system, for example by a processor.

The exemplary embodiments of the present invention described above in this description are also to be understood as being disclosed in all combinations with one another.

In particular, is intended by the preceding and following description of method steps according to the different embodiments of the method to also disclose corresponding means for performing the method steps by preferred embodiments of the other aspects (such as the system). Likewise, the disclosure of means for carrying out a method step are also intended to disclose the corresponding method step.

Further advantageous exemplary embodiments of the invention are indicated in the following detailed description of some exemplary embodiments of the present invention, in particular in conjunction with the figures. The figures should, however, serve only for the purpose of clarification, not for determining the scope of the invention. The figures are not to scale and are merely intended to exemplify the general concept of the present invention. In particular, features included in the figures are by no means intended to be considered as a necessary part of the present invention.

DETAILED DESCRIPTION

Figure 1:
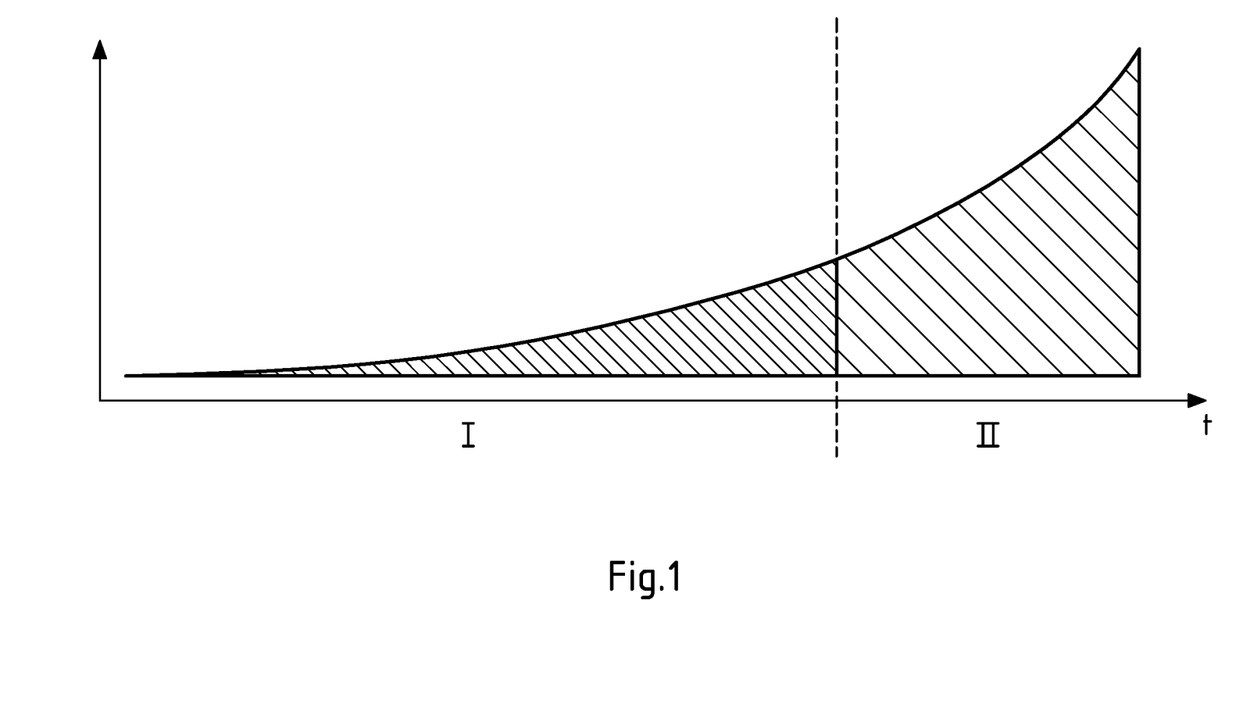
FIG. 1 shows a diagram for schematically illustrating the (undiscovered) growth of a neoplasia.

FIG. 1 shows first a diagram 100 for the schematic illustration of the undetected growth of a neoplasia, wherein the (clonal) growth in a haematological neoplasia is plotted over time. Growth initially goes unnoticed (Phase I) and leads only at an advanced stage (Phase II) to tangible disease symptoms that manifest clinically. Even then, however, the symptoms and laboratory findings are non-specific and hardly distinguishable from those of much more common diseases. The invention now makes it possible to provide both in Phase I and in Phase II an effective and efficient screening method for the detection of blood cancer.

The invention will be described in more detail below on the basis of FIGS. 2 and 3, which provide a schematic representation of an embodiment of a system 200 or a method 300 according to the invention.

Figure 2:
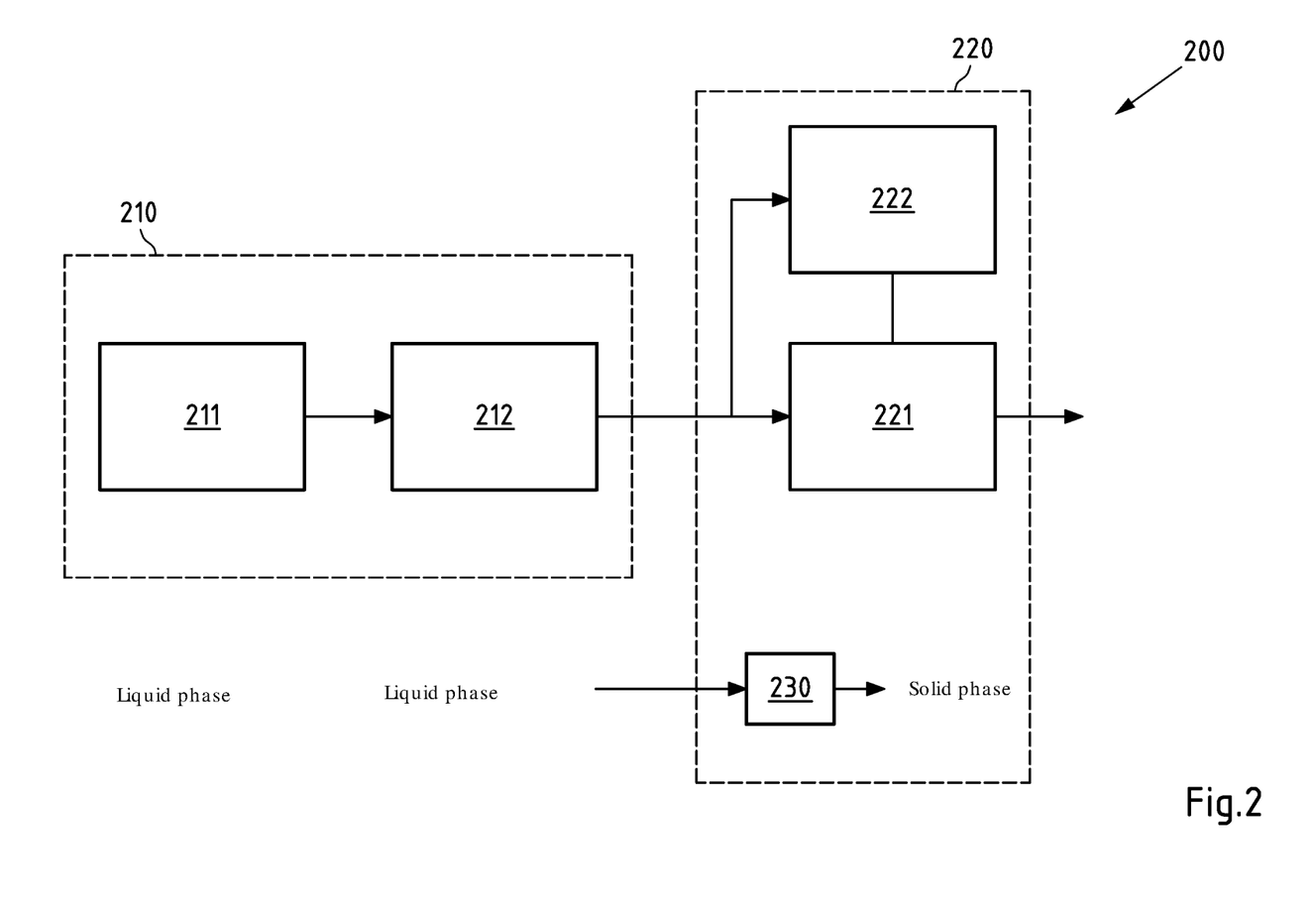
FIG. 2 shows a schematic representation of an exemplary embodiment of a system according to the invention.
Figure 3:
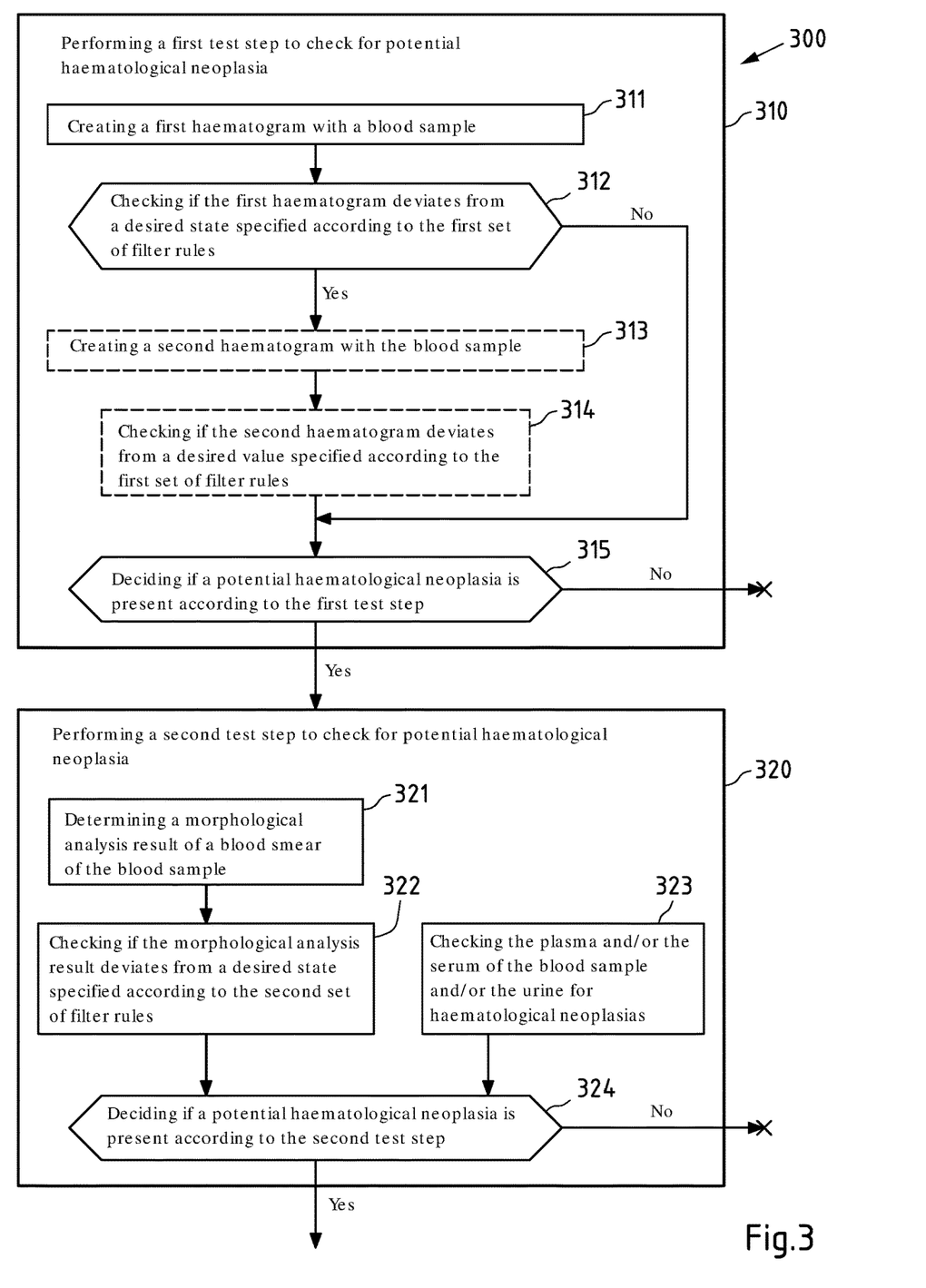
FIG. 3 shows a flow chart of an embodiment of a method according to the invention.

FIG. 2 first illustrates the division of the system 200 into two test steps 210 and 220. The first test step 210 comprises two cell analysers 211, 212 (first automatic cell analyser 211 and second automatic cell analyser 212) and is based on an analysis of the blood sample in the liquid phase. The second test step 220 includes a digital cell morphology analyser 221 and is based on an analysis of the blood sample in the solid phase, that is, blood cells that have been placed on a slide, e.g. in the form of a blood smear or by means of a nozzle. Such a blood cell solid phase carrier can be made, for example, by device 230 for automatic preparation of a blood cell solid phase carrier. In addition, the second test step 220 here comprises an analysis device 222 for testing the plasma and/or the serum of the blood sample and/or the urine.

First, a check is made with a blood sample in a first test step of whether there is a potential haematological neoplasia (action 310). For this purpose, a blood sample is supplied to a first automatic cell analyser 211 of the first test step 210. Firstly, the blood sample is used to create a first haematogram (for example, a small blood count) (action 311).

Subsequently, a check is made of whether the first haematogram deviates from a desired state specified according to a first set of filter rules (action 312).

The first set of filter rules comprises the following four filter rules:

| Filter rule 1 | 'Abnormal lymphocytes' value | >0 |
| | OR, 'immature granulocytes' value | >0 |
| | OR blast value | >0 |
| Filter rule 2 | Leucocytes value | >50,000/μL |
| Filter rule 3 | Platelets value | <100,000/μL |
| | AND haemoglobin value | <10.6 g/dl (female/unknown) <12.1 g/dl (male) |
| Filter rule 4 | Monocytes value | >1,500/μL |

The above inequalities in this case indicate when there is a deviation according to a filter rule. In this case, it is decided that the first haematogram deviates from the desired state specified according to the first set of filter rules if the first haematogram already deviates from a desired state specified according to a single filter rule of the four filter rules.

If the first haematogram does not deviate, the procedure can be terminated.

If the first haematogram deviates from the desired state specified according to the first set of filter rules, a second haematogram is also created with the blood sample (for example, a complete blood count), which has a higher accuracy than the first haematogram (action 313). This is done by means of the automatic cell analyser 212 of the first test step 210. It is then checked again based on the first set of filter rules, whether the second haematogram deviates from the desired state specified according to the first set of filter rules (action 314).

If this is not the case, it can be decided that no potential haematologic neoplasia is present (action 315). The procedure can be terminated. If this is the case, however, it can be decided that there is a potential haematological neoplasia in the first test step (action 315).

This results in a second test step being performed to check for potential haematological neoplasia (action 320). In the second test step, however, only about 1% of the original samples have to be analysed, as approximately 99% of the samples could already be filtered out by the first test step.

The actions 313, 314 may also be omitted in an exemplary embodiment. In that case, action 315 will then decide whether there is potential haematological neoplasia based on the examination of the first haematogram (action 312).

For this purpose, a blood cell solid phase carrier is made by means of a device 230 for automatic preparation of a blood cell solid phase carrier. As part of the second test step 220, a morphological analysis result of the solid phase of the blood sample is then determined (action 321). On the basis of a second set of filter rules a check is made of whether the morphological analysis result of the second test step deviates from a desired state specified according to the second set of filter rules.

The second set of filter rules comprises the following ten filter rules, each with a threshold in relation to 100 counted nucleated cells:

| Filter rule 5 | Shadow cell | >10 |
| Filter rule 6 | 'Likely reactive atypical lymphocytes' value | >15 |
| Filter rule 7 | Lymphocytes value | >70 |

-continued

| Filter rule 8 | 'Unclear and/or neoplastic lymphocytes' value | ≥1 |
| Filter rule 9 | Monocytes value | ≥20 |
| Filter rule 10 | 'Basophilic granulocytes' value | >5 |
| Filter rule 11 | Myelocytes value | >5 |
| Filter rule 12 | Promyelocytes value | ≥3 |
| Filter rule 13 | Blast value | ≥3 |
| Filter rule 14 | Normoblasts value | ≥5 |

The above inequalities in this case indicate when there is a deviation according to a filter rule. It is then checked if the morphological analysis result deviates from the desired state specified by the second set of filter rules (action 322). This is the case when the morphological analysis result already deviates from a desired state specified by a single filter rule of the ten filter rules.

If the morphological analysis result does not deviate from the specified desired state, it can be decided that there is no potential haematological neoplasia (action 324). In this case the procedure can be terminated. However, if the morphological analysis result does deviate from the specified desired state, it can be decided in action 324 that there is a potential haematological neoplasia.

Optionally, in addition, as part of the second test step 220, by means of an analysis device 222 the plasma and/or serum of the blood sample and/or urine will again be tested for haematological neoplasia (action 323) if a corresponding sample is available. The result of the examination of the plasma and/or serum and/or the urine can, for example, influence the decision in action 324 on whether there is a potential haematological neoplasia. Alternatively, the result may also only be made available for method steps further downstream.

If it is decided in action 324 that there is no potential haematological neoplasia, the procedure can be terminated. However, if it is decided in action 324 that there is a potential for haematological neoplasia, further method steps, such as further manual or automated analysis, may be performed to provide a conclusive finding.

However, the further method steps only have to be carried out for about 2% of the samples passing through the second test step, i.e. only for about 0.02% of the samples originally to be investigated.

Figure 4:
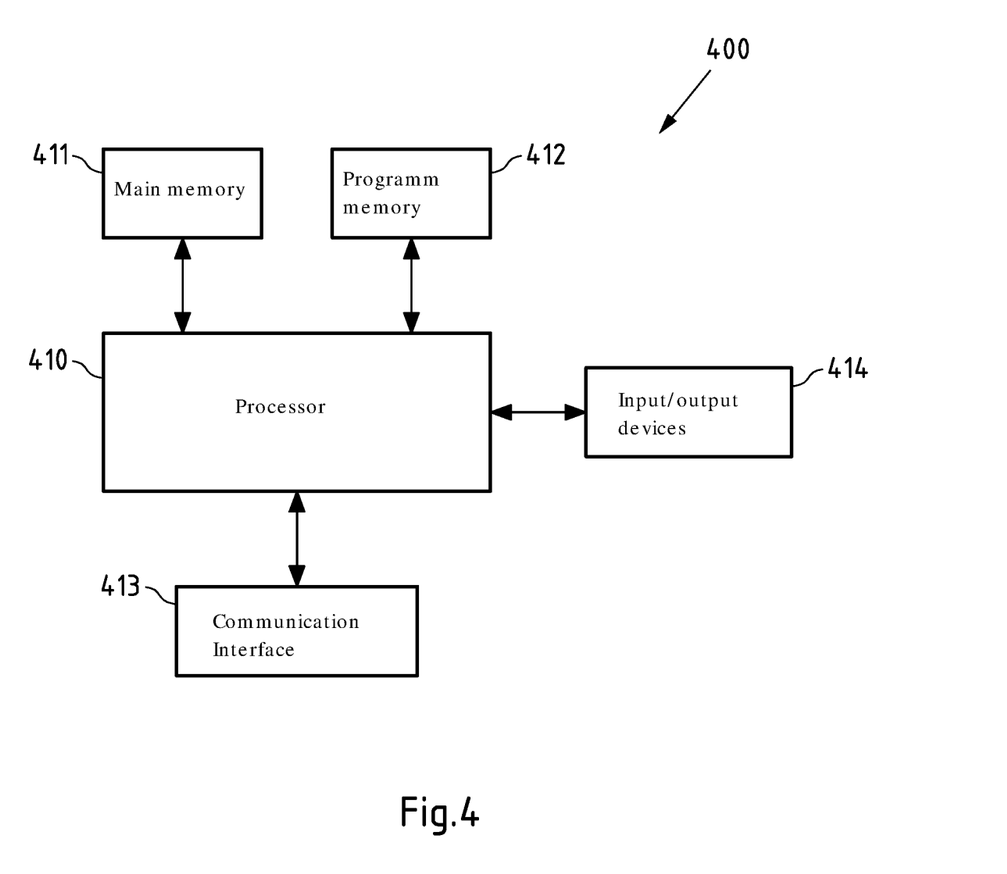
FIG. 4 shows a block diagram of an exemplary device of an exemplary embodiment of a system according to the invention.

Finally, FIG. 4 shows a block diagram of an exemplary device 400, such as may be used in the system 200, for example as a device 211, 212, 221, 222 and/or 230.

The device 400 may be or include, for example, a data processing system.

Processor 410 of device 400 is in particular a microprocessor, micro-control unit, microcontroller, digital signal processor (DSP), Application Specific Integrated Circuit (ASIC) or Field Programmable Gate Array (FPGA).

Processor 410 executes program instructions stored in program memory 412 and stores, for example, intermediate results or the like in working or main memory 411. For example, program memory 412 is a non-volatile memory such as a flash memory, magnetic memory, EEPROM memory (electrically erasable programmable read only memory) and/or optical memory. Main memory 411 is, for example, a volatile or non-volatile memory, in particular a random access memory (RAM) such as a static RAM (SRAM), a dynamic RAM (DRAM), a ferroelectric RAM (FeRAM). and/or a magnetic RAM memory (MRAM).

Program memory 412 is preferably a local data carrier permanently attached to device 400. Data carriers permanently connected to the device 400 are, for example, hard disks which are built into the device 400. Alternatively, the data carrier can also be, for example, a data carrier that is separably connectable to the device 400 such as a memory stick, a removable disk, a portable hard disk, a CD, a DVD and/or a floppy disk.

Program memory 412 includes, for example, the operating system of the device 400, which upon starting of the device 400 is at least partially loaded into the main memory 411 and executed by the processor 410. In particular, when starting device 400, at least a portion of the core of the operating system is loaded into the main memory 411 and executed by processor 410.

The operating system in particular allows the use of the device 400 for data processing. It manages, for example, resources such as main memory 411 and program memory 412, network interface 413, input and output device 414, provides basic functions to other programs through programming interfaces, among other things, and controls the execution of programs.

Processor 410 controls communication interface 413, which may be, for example, a network interface and may be in the form of a network card, network module and/or modem. The communication interface 413 is in particular configured to establish a connection of the device 400 with other devices, in particular via a (wireless) communication system, for example a network, and to communicate with these, for example other devices of the system 200. The communication interface 413 can, for example, (via the communication system) receive data and forward it to processor 410 and/or receive data from processor 410 and send it (via the communication system). Examples of a communication system are a local area network (LAN), a wide area network (WAN), a wireless network (for example, according to the IEEE 802.11 standard, the Bluetooth (LE) standard and/or the NFC standard), a wired network, a mobile network, a telephone network and/or the Internet.

Furthermore, processor 410 may control at least one input/output device 414. Input/output device 414 is, for example, a keyboard, a mouse, a display unit, a microphone, a touch-sensitive display unit, a loudspeaker, a reading device, a drive and/or a camera. The input/output device 414 can, for example, receive user input and forward it to processor 410 and/or receive and output information for the user of processor 410.

Finally, a corresponding device can also have further means which can be used for method steps in the context of the method according to the invention, such as, for example, analysis units for the automated production of a haematogram or a digital morphological analysis.

The exemplary embodiments of the present invention described in this specification and the respective optional features and properties cited in this context should also be understood to be disclosed in all combinations with one another. In particular, the description of a feature incorporated by an exemplary embodiment—unless explicitly stated to the contrary—should in the present case not be taken to mean that the feature is indispensable or essential to the operation of the embodiment. The sequence of method steps described in this specification in the individual flow diagrams is not imperative; alternative sequences of the method steps are conceivable. The method steps can be implemented in various ways, so an implementation in software (by way of program instructions), hardware or a combination of the two is conceivable for implementing the method steps. Terms used in the claims such as "comprise", "have", "include". "contain" and the like do not rule out additional elements or steps. The phrase "at least partially" covers both "partially" and "completely". The phrase "and/or" shall be understood to mean that both the alternatives and combination are disclosed, thus "A and/or B" shall mean "(A) or (B) or (A and B)". The use of the indefinite article does not rule out a plurality A single device can carry out the functions of a plurality of the units or apparatuses mentioned in the claims Reference numerals specified in the claims should not be regarded as limitations on the means and steps used.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A mass screening method for diagnosis of haematological neoplasia, at least in part performed in an automated manner by a system, comprising the steps of:
performing a first test step to check for potential haematological neoplasia, wherein the first test step is performed partially or fully automated, wherein as part of the first test step at least a first haematogram is created with a blood sample in the liquid phase and it is checked based on a first set of filter rules whether the first haematogram deviates from a desired state specified according to the first set of filter rules, and wherein the first set of filter rules comprises at least two filter rules, wherein the at least first haematogram comprises a haemoglobin value and a platelets value, and wherein a filter rule of the first set of filter rules of the first test step is based on the haemoglobin value and the platelets value, and performing a second test step to check for potential haematological neoplasia if the first test step indicates that there is potential haematological neoplasia, wherein the second test step is partially or completely automated, wherein as part of the second test step a morphological analysis result of a solid phase of the blood sample is determined and it is checked based on a second set of filter rules whether the morphological analysis result of the second test step deviates from a desired state specified according to the second set of filter rules, and wherein the second set of filter rules comprises at least two filter rules;

deciding whether there is a haematological neoplasia at least based on at least one or the first test step and the second test step.

2. The screening method according to claim 1, wherein as part of the first test step, if the first haematogram deviates from the desired state specified according to the first set of filter rules, a second haematogram, which has a higher accuracy than the first, is created with the blood sample, and based on the first set of filter rules it is checked whether the second haematogram deviates from the desired state specified according to the first set of filter rules.

3. The screening method according to claim 1, wherein the at least first haematogram deviates from the desired state specified according to the first set of filter rules already when the at least first haematogram deviates from a desired state specified according to a filter rule of the first set of filter rules.

4. The screening method according to claim 1, wherein the at least first haematogram comprises an 'abnormal lymphocytes' value, an 'immature granulocytes' value and/ or a blast value, and wherein a filter rule of the first set of filter rules of the first test step is based on the 'abnormal lymphocytes' value, the 'immature granulocytes' value and/ or the blast value.

5. The screening method according to claim 1, wherein the at least first haematogram comprises a leucocytes value, and wherein a filter rule of the first set of filter rules of the first test step is based on the leucocytes value.

6. The screening method according to claim 5, wherein the at least first haematogram deviates from the desired state specified according to the filter rule of the first test step based on the leucocytes value when the leucocytes value is above a threshold or corresponds to this.

7. The screening method according to claim 1, wherein the at least first haematogram deviates from the desired state specified according to the filter rule based on the haemoglobin value and platelets value of the first test step, if the haemoglobin value is below a threshold or corresponds to this and the platelets value is below or corresponds to a threshold value.

8. The screening method according to claim 7, wherein the threshold for the haemoglobin value is a gender-specific threshold.

9. The screening method according to claim 1, wherein the at least first haematogram comprises a monocytes value, and wherein a filter rule of the first set of filter rules of the first test step is based on the monocytes value.

10. The screening method according to claim 9, wherein the at least first haematogram deviates from the desired state specified according to the filter rule of the first test step based on the monocytes value, when the monocytes value is above a threshold or corresponds to this.

11. The screening method according to claim 1, wherein the morphological analysis result of the second test step already deviates from the desired state specified according to the second set of filter rules if the morphological analysis result of the second test step deviates from a desired state specified according to a filter rule of the second set of filter rules.

12. The screening method according to claim 1, wherein the morphological analysis result of the second test step comprises one or more cell type values, particularly of nucleated cell types, and wherein one or more filter rules of the second set of filter rules of the second test step are each based on at least one, in particular, exactly one cell type value.

13. The screening method according to claim 12, wherein the morphological analysis result of the second test step deviates from the desired state specified by a filter rule based on a cell-type value of the second test step if the respective cell-type value is greater than or equal to a respective threshold.

14. The screening method according to claim 12, wherein one or more of the cell type values are based on the following cell types:
   shadow cells;
   likely reactive atypical lymphocytes;
   lymphocytes;
   unclear and/or neoplastic lymphocytes;
   monocytes;
   basophilic granulocytes;
   myelocytes;
   promyelocytes;
   blasts; or
   normoblasts.

15. The screening method according to claim 1, wherein the second test step involves testing the plasma and/or serum of the blood sample and/or urine for haematological neoplasia.

16. A system which is configured or comprises corresponding means for carrying out and/or controlling a method according to claim 1.

17. The system according to claim 16, wherein the system comprises at least one processor and at least one memory with computer program code, wherein the at least one memory and the computer program code are configured to at least execute and/or control the process with the at least one processor.

18. A non-transitory computer readable storage medium containing a computer program product comprising program instructions for carrying out a method according to claim 1 when the program instructions are executed on a processor.

* * * * *